(12) United States Patent
Chen et al.

(10) Patent No.: US 8,128,579 B2
(45) Date of Patent: Mar. 6, 2012

(54) GUIDEWIRES WITH IMPROVED FATIGUE LIFE AND METHODS OF MAKING THE SAME

(75) Inventors: Hancun Chen, Maple Grove, MN (US); Peter Skujins, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1060 days.

(21) Appl. No.: 11/934,659

(22) Filed: Nov. 2, 2007

(65) Prior Publication Data

US 2009/0118705 A1    May 7, 2009

(51) Int. Cl.
*A61B 5/00* (2006.01)

(52) U.S. Cl. ......................................... 600/585; 604/525

(58) Field of Classification Search .................. 600/585; 604/525; 164/1
See application file for complete search history.

(56) References Cited

U.S. PATENT DOCUMENTS

| | | | |
|---|---|---|---|
| 4,763,667 A | 8/1988 | Manzo | |
| 5,055,101 A * | 10/1991 | McCoy | 604/528 |
| 5,152,748 A * | 10/1992 | Chastagner | 604/95.05 |
| 5,213,111 A | 5/1993 | Cook et al. | |
| 5,772,609 A | 6/1998 | Nguyen et al. | |
| 6,039,699 A | 3/2000 | Viera | |
| 6,139,510 A | 10/2000 | Palermo | |
| 6,329,069 B1 | 12/2001 | Azizi et al. | |
| 6,497,709 B1 | 12/2002 | Heath | |
| 6,520,923 B1 | 2/2003 | Jalisi | |
| 7,074,197 B2 * | 7/2006 | Reynolds et al. | 600/585 |
| 7,182,735 B2 | 2/2007 | Shireman et al. | |
| 2002/0043118 A1 | 4/2002 | Claude | |
| 2002/0142119 A1 | 10/2002 | Seward et al. | |
| 2002/0165600 A1 | 11/2002 | Banas et al. | |
| 2003/0216668 A1 | 11/2003 | Howland et al. | |
| 2007/0200656 A1 * | 8/2007 | Walak | 337/333 |

FOREIGN PATENT DOCUMENTS

| | | |
|---|---|---|
| JP | 11000400 | 1/1999 |
| WO | 93/19803 | 10/1993 |
| WO | 2005/044358 | 5/2005 |
| WO | 2007/131766 | 11/2007 |

* cited by examiner

*Primary Examiner* — Max Hindenburg
*Assistant Examiner* — Renee Danega
(74) *Attorney, Agent, or Firm* — Seager, Tufte & Wickhem, LLC (57) ABSTRACT

A medical device, such as a medical guidewire, having a portion including an inner zone of material and an outer peripheral zone of material surrounding the inner zone of material. The inner zone of material has a first coefficient of thermal expansion and the outer peripheral zone of material has a second coefficient of thermal expansion less than the first coefficient of thermal expansion, wherein at an operating temperature the outer peripheral zone of material opposes expansion of the inner zone of material such that the outer peripheral zone of material exerts a compressive stress on the inner zone of material.

14 Claims, 9 Drawing Sheets

GUIDEWIRES WITH IMPROVED FATIGUE LIFE AND METHODS OF MAKING THE SAME

TECHNICAL FIELD

The present disclosure generally relates to medical devices, and more particularly pertains to guidewires having improved fatigue life and methods of making the same.

BACKGROUND

During medical procedures, guidewires are routinely subjected to various mechanical stresses and/or aqueous fluid while positioned within the vasculature of a patient. For example, when the guidewire is constrained inside a tortuous blood vessel, the distal portion of the guidewire may bend, thus inducing an in-plane bending stress on the guidewire. In some instances in which the distal portion of the guidewire remains in the tortuous blood vessel, the guidewire may experience cyclic stresses. These cyclic stresses may, for example, have a frequency equal to the heart beat rate of the patient. The generated cyclic stresses may lead to crack initiation at the surface of the guidewire and subsequent crack propagation. Thus, the cyclic stresses experienced by the guidewire may diminish the fatigue life of the guidewire, resulting in premature fatigue failure of the guidewire. Exposure of the guidewire to aqueous fluids may additionally accelerate fatigue failure of the guidewire.

SUMMARY

The present disclosure is directed to medical devices such as guidewires, or the like, and/or methods of forming medical devices such as guidewires, or the like, which improve the fatigue life of the medical device.

Accordingly, one illustrative embodiment is a medical device, such as a medical guidewire, having a portion including an inner zone of material and an outer peripheral zone of material surrounding the inner zone of material. The inner zone of material has a first coefficient of thermal expansion, and the outer peripheral zone of material has a second coefficient of thermal expansion less than the first coefficient of thermal expansion, wherein at an operating temperature the outer peripheral zone of material opposes expansion of the inner zone of material such that the outer peripheral zone of material exerts a compressive stress on the inner zone of material.

Another illustrative embodiment is a medical device, such as a medical guidewire, having a portion including an inner zone of material and an outer peripheral zone of material metallurgically bonded to the inner zone of material along an interface between the inner zone of material and the outer peripheral zone of material. The inner zone of material having a first coefficient of thermal expansion and the outer peripheral zone of material having a second coefficient of thermal expansion less than the first coefficient of thermal expansion, wherein at a first temperature the outer peripheral zone of material exerts approximately zero or negligible residual compressive stress on the inner zone of material, and at a second temperature greater than the first temperature the outer peripheral zone of material exerts a residual compressive stress on the inner zone of material.

Yet another illustrative embodiment is a medical device, such as a medical guidewire, including an elongate shaft extending between a proximal end and a distal end. The elongate shaft includes a sub-surface portion comprising a first material having a first coefficient of thermal expansion, and a second material surrounding the first material, the second material having a second coefficient of thermal expansion. The first coefficient of thermal expansion is selected to be greater than the second coefficient of thermal expansion such that at an operating temperature the elongate shaft is subjected to a compressive stress at a sub-surface location proportional to the difference between the first coefficient of thermal expansion and the second coefficient of thermal expansion.

A further illustrative embodiment is a method of increasing the fatigue life of a medical device, such as a medical guidewire. The method includes the steps of providing a guidewire including an inner zone of material having a first coefficient of thermal expansion, and an outer peripheral zone of material having a second coefficient of thermal expansion less than the first coefficient of thermal expansion. Upon exposing the guidewire to an operating temperature, the outer peripheral zone of material opposes expansion of the inner zone of material such that the outer peripheral zone of material exerts a compressive stress on the inner zone of material.

Yet another illustrative embodiment is a method of increasing the fatigue life of a medical device, such as a medical guidewire. The method includes the steps of providing an elongate shaft including a first material having a first coefficient of thermal expansion and metallurgically bonding a second material to the first material. The second material has a second coefficient of thermal expansion less than the first coefficient of thermal expansion; such that at a first temperature the second material exerts approximately zero or negligible compressive stresses on the first material, and at a second temperature greater than the first temperature the second material opposes expansion of the first material, thereby exerting a compressive stress on the first material.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Figure 1:
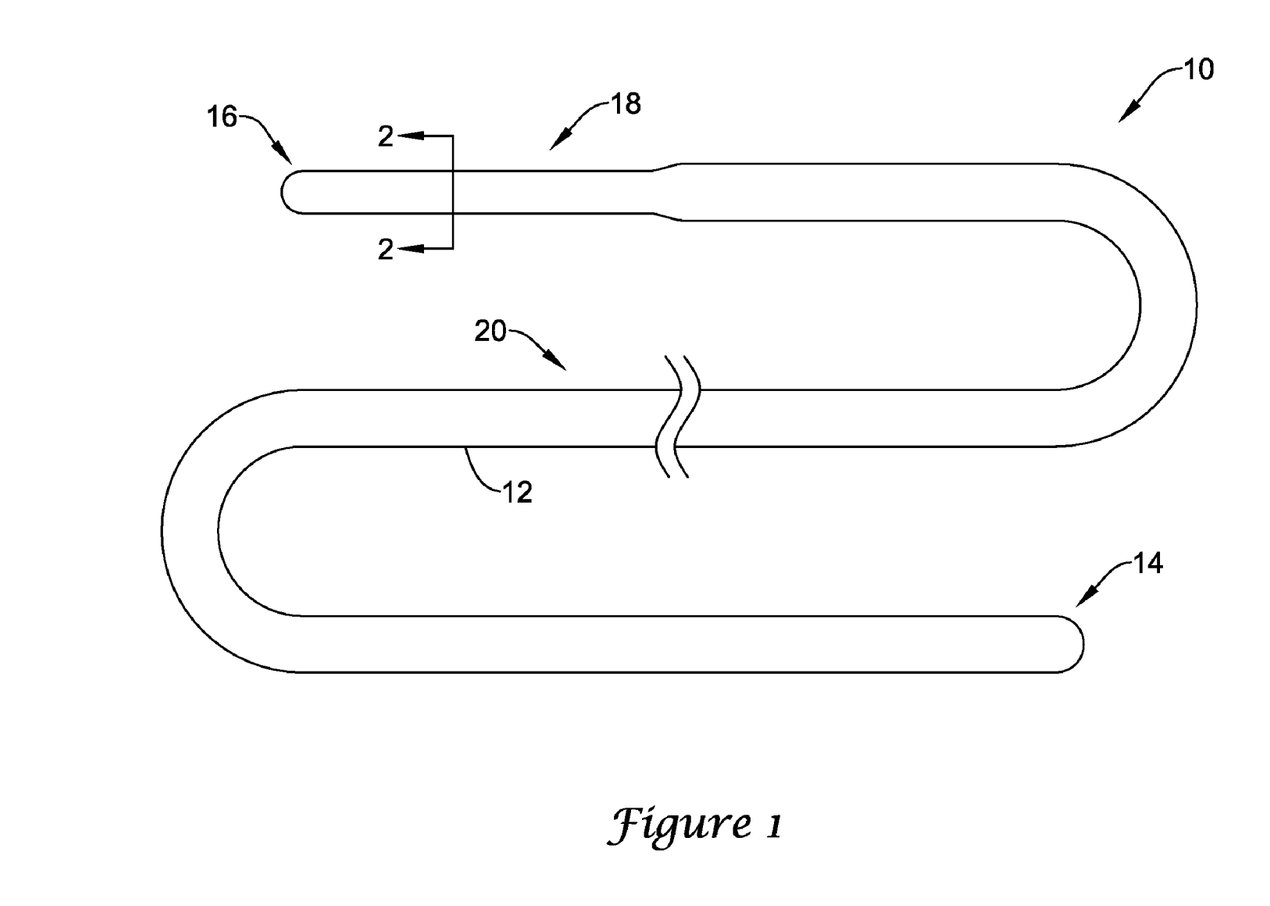
FIG. 1 is a plan view of an exemplary guidewire.

Referring now to FIG. 1, an exemplary medical device illustrated as a medical guidewire 10 is shown. The guidewire 10 may include an elongate shaft 12, such as a core wire, extending from a proximal end 14 to a distal end 16. The guidewire 10 may be any suitable length. For example, the guidewire 10 may have a length of about 25 cm or greater, about 50 cm or greater, about 100 cm or greater, about 150 cm or greater, or 200 cm or greater in some instances. The guidewire 10 may include a distal portion 18 proximate the distal end 16 and a proximal portion 20 proximal of the distal portion 18. In some embodiments, such as that illustrated in FIG. 1, the distal portion 18 may be a reduced diameter portion of the guidewire 10. In other words, the distal portion 18 may have an outer diameter less than the outer diameter of the proximal portion 20 proximal of the distal portion 18. For example, the distal portion 18 may include a reduced diameter portion of the elongate shaft 12, such as a reduced diameter portion of a core wire. In some embodiments, the guidewire 10 may include one or more additional portions, which may or may not be reduced diameter portions, as desired.

Figure 2A:
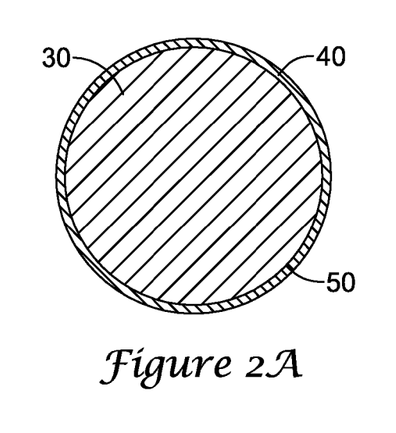
FIGS. 2A-2C are alternative cross-sectional views of a portion of the guidewire of FIG. 1 taken along line 2-2 of FIG. 1.

FIG. 2A depicts an exemplary cross-section of the distal portion 18 of the guidewire 10 taken along a plane perpendicular to the longitudinal axis of the guidewire 10 along line 2-2 of FIG. 1. However, in some embodiments, the cross-section shown in FIG. 2A may exemplify a cross-section taken at another location along the length of the elongate shaft 12. As shown in FIG. 2A, the guidewire 10 may include an inner zone of material 30 surrounded by an outer peripheral zone of material 40. In some embodiments, the outer peripheral zone of material 40 may fully encircle the inner zone of material 30. The outer peripheral zone of material 40 may be uniformly or non-uniformly distributed about the inner zone of material 30. In other embodiments, the outer zone of material 40 may be located at one or more select radial locations, thus not fully encompassing the inner zone of material 30.

The inner zone of material 30 may extend along the entire length of the guidewire 10, substantially the entire length of the guidewire 10, throughout the distal portion 18 of the guidewire 10, or any other desired portion of the guidewire 10. The inner zone of material 30 may be formed of any of various materials. For example, the inner zone of material 30 may be a metallic material, such as a metal or metal alloy. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof, and the like; or any other suitable material.

The outer zone of material 40 may extend along the entire length of the guidewire 10, substantially the entire length of the guidewire 10, throughout the distal portion 18 of the guidewire 10, or any other desired portion of the guidewire 10. For instance, in some embodiments, the outer zone of material 40 may extend proximally from the distal end 16 of the guidewire for about 15 cm or less, about 10 cm or less, about 5 cm or less, or about 3 cm or less. In some embodiments, the thickness of the outer zone of material 40 may be about 2 nanometers or more, about 5 nanometers or more, about 10 nanometers or more, about 25 nanometers or more, or about 50 nanometers or more, for example. In some embodiments, the thickness of the outer zone of material 40 may be about 2 micrometers or less, about 1 micrometer or less, about 500 nanometers or less, about 100 nanometers or less, about 50 nanometers or less, about 25 nanometers or less, or about 10 nanometers or less, for example. In some embodiments, the thickness of the outer zone of material 40 may be in the range of about 2 nanometers to about 2 micrometers, in the range of about 2 nanometers to about 1 micrometer, in the range of about 2 nanometers to about 500 nanometers, in the range of about 2 nanometers to about 100 nanometers, in the range of about 5 nanometers to about 1 micrometer, in the range of about 5 nanometers to about 500 nanometers, or in the range of about 5 nanometers to about 100 nanometers, for example. Although some suitable dimensions are disclosed, one of skill in the art, incited by the present disclosure, would understand desired dimensions may deviate from those expressly disclosed. The outer zone of material 40 may be any of various materials. For example, the outer zone of material 40 may be a metallic material, such as a metal or metal alloy. For instance, the outer zone of material 40 may be a biocompatible material such as titanium or a titanium alloy, tungsten or a tungsten alloy, tantalum or a tantalum alloy, chromium or a chromium alloy, niobium or a niobium alloy, zirconium or a zirconium alloy, platinum or a platinum alloy, combinations thereof, and the like, or any other suitable material including those materials listed above.

As shown in FIG. 2A, the inner zone of material 30 is chosen to have a coefficient of thermal expansion greater than the coefficient of thermal expansion of the outer zone of material 40. For instance, the coefficient of thermal expansion of the inner zone of material 30 may be about $10 \times 10^{-6}/°$ C. to about $18 \times 10^{-6}/°$ C., or about $10 \times 10^{-6}/°$ C. to about $14 \times 10^{-6}/°$ C., or about $10 \times 10^{-6}/°$ C. to about $12 \times 10^{-6}/°$ C., or about $14 \times 10^{-6}/°$ C. to about $18 \times 10^{-6}/°$ C., or about $16 \times 10^{-6}/°$ C. to about $18 \times 10^{-6}/°$ C. Likewise, the coefficient of thermal expansion of the outer zone of material 40 may be about $4 \times 10^{-6}/°$ C. to about $14 \times 10^{-6}/°$ C., about $6 \times 10^{-6}/°$ C. to about $12 \times 10^{-6}/°$ C., or about $8 \times 10^{-6}/°$ C. to about $10 \times 10^{-6}/°$ C., about $4 \times 10^{-6}/°$ C. to about $5 \times 10^{-6}/°$ C., about $5 \times 10^{-6}/°$ C. to about $6 \times 10^{-6}/°$ C., about $6 \times 10^{-6}/°$ C. to about $7 \times 10^{-6}/°$ C., about $7 \times 10^{-6}/°$ C. to about $8 \times 10^{-6}/°$ C., about $8 \times 10^{-6}/°$ C. to about $9 \times 10^{-6}/°$ C., or about $9 \times 10^{-6}/°$ C. to about $10 \times 10^{-6}/°$ C., for example. In some embodiments the difference between the coefficient of thermal expansion of the inner zone of material 30 and the coefficient of thermal expansion of the outer zone of material 40 may be about $2 \times 10^{-6}/°$ C. to about $10 \times 10^{-6}/°$ C., or about $2 \times 10^{-6}/°$ C. to about $4 \times 10^{-6}/°$ C., or about $4 \times 10^{-6}/°$ C. to about $5 \times 10^{-6}/°$ C., or about $5 \times 10^{-6}/°$ C. to about $7 \times 10^{-6}/°$ C., or about $7 \times 10^{-6}/°$ C. to about $9 \times 10^{-6}/°$ C., for example.

In one perceived embodiment, the inner zone of material 30 may be formed of a stainless steel alloy such as SS304 having a coefficient of thermal expansion (TEC) of about $17 \times 10^{-6}/°$ C. or nitinol having a TEC of about $11 \times 10^{-6}/°$ C. and the outer zone of material 40 may be formed of titanium having a TEC of about $9 \times 10^{-6}/°$ C. or a titanium alloy (e.g., Ti-6Al-4V having about 5.5-6.5% aluminum, 3.5-4.5% vanadium and less than about 0.5% other metals with the balance being titanium designated as UNS: R56400) having a TEC of about $8.6 \times 10^{-6}/°$ C.

An interface 50 may be defined between the inner zone of material 30 and the outer peripheral zone of material 40 at a subsurface location of the elongate shaft 12. The outer zone of material 40 may be metallurgically or metallically bonded to the inner zone of material 30 at the interface 50. A metallurgical or metallic bond is distinguishable from other types of bonds, such as mechanical bonds, covalent bonds, and ionic bonds. A metallurgical bond is achieved when atoms of two materials interact at the atomic or molecular level such that atoms of each material share electrons with atoms of the other material, forming an electron sea. A metallurgical bond is an omnidirectional, non-polar bond which involves the delocalized sharing of free electrons among a lattice of positively charged metal atoms known as kernels. Thus, a metallurgical bond is distinguishable from a covalent or ionic bond. It is believed that an attractive force is present at the interface between the positively charged metal atoms or kernels of the bonded materials and the delocalized electrons, fusing the materials together. Dissimilarly, a mechanical bond is achieved by the interaction of the surface roughness of the bonded materials in which delocalized sharing of free electrons is not present. For example, a drawing process may result in a mechanical bond between two materials. Materials joined by a mechanical bond may be amenable to separation when subjected to bending, whereas materials which are metallurgically bonded may remain bonded together when subjected to bending. This may be explained by the fact that the positively charged cations, called kernels, may shift around on the layer of electrons, but because of the delocalized nature of the electrons, the omnidirectional bonds will not break.

The outer zone of material 40 may be metallurgically bonded to the inner zone of material 30 in various ways. For example, the outer zone of material 40 may be metallurgically bonded to the inner zone of material 30 through a physical vapor deposition process, a chemical vapor deposition process, a plasma-enhanced chemical vapor deposition process, a cold spray process, a hot spray process, an electroplating process, or the like.

Figure 2B:
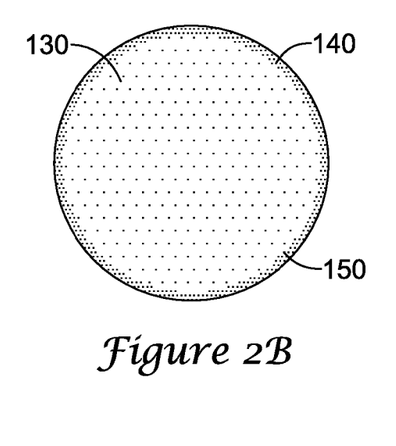

FIG. 2B depicts an alternative cross-section of the distal portion 18 of the guidewire 10 taken along a plane perpendicular to the longitudinal axis of the guidewire 10 along line 2-2 of FIG. 1. However, in some embodiments, the cross-section shown in FIG. 2B may exemplify a cross-section taken at another location along the length of the elongate shaft 12. As shown in FIG. 2B, the guidewire 10 may include an inner zone of material 130 surrounded by an outer peripheral zone of material 140. In some embodiments, the outer peripheral zone of material 140 may fully encircle the inner zone of material 130. The outer peripheral zone of material 140 may be uniformly or non-uniformly distributed about the inner zone of material 130. In other embodiments, the outer zone of material 140 may be located at one or more select radial locations, thus not fully encompassing the inner zone of material 130.

The inner zone of material 130 may extend along the entire length of the guidewire 10, substantially the entire length of the guidewire 10, throughout the distal portion 18 of the guidewire 10, or any other desired portion of the guidewire 10. The outer zone of material 140 may extend along the entire length of the guidewire 10, substantially the entire length of the guidewire 10, throughout the distal portion 18 of the guidewire 10, or any other desired portion of the guidewire 10. For instance, in some embodiments, the outer zone of material 140 may extend proximally from the distal end 16 of the guidewire for about 15 cm or less, about 10 cm or less, about 5 cm or less, or about 3 cm or less. In some embodiments, the thickness of the outer zone of material 140 may be about 2 nanometers or more, about 5 nanometers or more, about 10 nanometers or more, about 25 nanometers or more, or about 50 nanometers or more, for example. In some embodiments, the thickness of the outer zone of material 140 may be about 2 micrometers or less, about 1 micrometer or less, about 500 nanometers or less, about 100 nanometers or less, about 50 nanometers or less, about 25 nanometers or less, or about 10 nanometers or less, for example. In some embodiments, the thickness of the outer zone of material 140 may be in the range of about 2 nanometers to about 2 micrometers, in the range of about 2 nanometers to about 1 micrometer, in the range of about 2 nanometers to about 500 nanometers, in the range of about 2 nanometers to about 100 nanometers, in the range of about 5 nanometers to about 1 micrometer, in the range of about 5 nanometers to about 500 nanometers, or in the range of about 5 nanometers to about 100 nanometers, for example.

Although some suitable dimensions are disclosed, one of skill in the art, incited by the present disclosure, would understand desired dimensions may deviate from those expressly disclosed.

The inner zone of material 130 and/or the outer zone of material 140 may be formed of any of various materials. For example, the inner zone of material 130 and/or the outer zone of material 140 may be a metallic material, such as a metal or metal alloy. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTEL-LOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; titanium and other titanium alloys (e.g., UNS: R56400 such as TIMETAL®, and the like); cobalt-chromium alloys; cobalt-chromium-molybdenum alloys (e.g., UNS: R30003 such as ELGILOY®, PHYNOX®, and the like); platinum enriched stainless steel; combinations thereof, and the like; or any other suitable material.

As shown in FIG. 2B, the inner zone of material 130 is chosen to have a coefficient of thermal expansion greater than the coefficient of thermal expansion of the outer zone of material 140. For instance, the coefficient of thermal expansion of the inner zone of material 130 may be about $10 \times 10^{-6}/°$ C. to about $18 \times 10^{-6}/°$ C., or about $10 \times 10^{-6}/°$ C. to about $14 \times 10^{-6}/°$ C., or about $10 \times 10^{-6}/°$ C. to about $12 \times 10^{-6}/°$ C., or about $14 \times 10^{-6}/°$ C. to about $18 \times 10^{-6}/°$ C., or about $16 \times 10^{-6}/°$ C. to about $18 \times 10^{-6}/°$ C. Likewise, the coefficient of thermal expansion of the outer zone of material 140 may be about $4 \times 10^{-6}/°$ C. to about $14 \times 10^{-6}/°$ C., about $6 \times 10^{-6}/°$ C. to about $12 \times 10^{-6}/°$ C., or about $8 \times 10^{-6}/°$ C. to about $10 \times 10^{-6}/°$ C., about $4 \times 10^{-6}/°$ C. to about $5 \times 10^{-6}/°$ C., about $5 \times 10^{-6}/°$ C. to about $6 \times 10^{-6}/°$ C., about $6 \times 10^{-6}/°$ C. to about $7 \times 10^{-6}/°$ C., about $7 \times 10^{-6}/°$ C. to about $8 \times 10^{-6}/°$ C., about $8 \times 10^{-6}/°$ C. to about $9 \times 10^{-6}/°$ C., or about $9 \times 10^{-6}/°$ C. to about $10 \times 10^{-6}/°$ C., for example. In some embodiments the difference between the coefficient of thermal expansion of the inner zone of material 130 and the coefficient of thermal expansion of the outer zone of material 140 may be about $2 \times 10^{-6}/°$ C. to about $10 \times 10^{-6}/°$ C., or about $2 \times 10^{-6}/°$ C. to about $4 \times 10^{-6}/°$ C., or about $4 \times 10^{-6}/°$ C. to about $5 \times 10^{-6}/°$ C., or about $5 \times 10^{-6}/°$ C. to about $7 \times 10^{-6}/°$ C., or about $7 \times 10^{-6}/°$ C. to about $9 \times 10^{-6}/°$ C., for example.

An interface 150 may be defined between the inner zone of material 130 and the outer zone of material 140. The interface 150 may be defined at a subsurface location of the elongate shaft 12 in which the molecular structure of the elongate shaft 12 transitions from the molecular structure of the inner zone of material 130 to the molecular structure of the outer zone of material 140. Thus, the inner zone of material 130 may have a molecular structure dissimilar from the molecular structure of the outer zone of material 140, yet the inner zone of material 130 may remain metallically bonded to the outer zone of material 140 such that a lattice of positively charged metal atoms known as kernels share delocalized electrons in an electron sea. For instance, the molecular structure of the material forming the elongate shaft 12 may be altered by one or more of various processes in order to form the outer zone of material 140 while leaving the molecular structure of the inner zone of material 130 unchanged. For example, the outer zone of material 140 may be formed during a heat treatment process, a diffusion process, case hardening process, or an oxidation process.

Figure 2C:
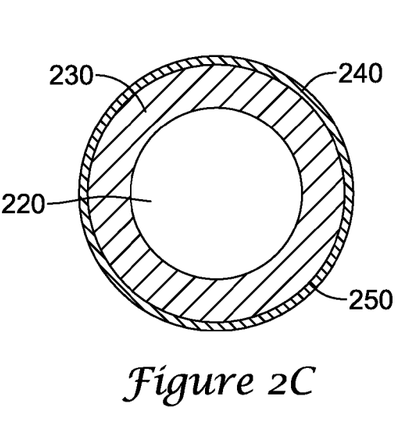

FIG. 2C depicts yet another alternative cross-section of the distal portion 18 of the guidewire 10 taken along a plane perpendicular to the longitudinal axis of the guidewire 10 along line 2-2 of FIG. 1. However, in some embodiments, the cross-section shown in FIG. 2C may exemplify a cross-section taken at another location along the length of the elongate shaft 12. As shown in FIG. 2C, the guidewire 10 may include a lumen 220 extending through the elongate shaft 12, thus the inner zone of material 230 may be an annular zone of material surrounded by the outer peripheral zone of material 240. In some embodiments, the outer peripheral zone of material 240 may fully encircle the inner zone of material 230. The outer peripheral zone of material 240 may be uniformly or non-uniformly distributed about the inner zone of material 230. In other embodiments, the outer zone of material 240 may be located at one or more select radial locations, thus not fully encompassing the inner zone of material 230.

The inner zone of material 230 may extend along the entire length of the guidewire 10, substantially the entire length of the guidewire 10, throughout the distal portion 18 of the guidewire 10, or any other desired portion of the guidewire 10. The inner zone of material 230 may be formed of any of various materials. For example, the inner zone of material 230 may be a metallic material, such as a metal or metal alloy. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof, and the like; or any other suitable material.

The outer zone of material 240 may extend along the entire length of the guidewire 10, substantially the entire length of the guidewire 10, throughout the distal portion 18 of the guidewire 10, or any other desired portion of the guidewire 10. For instance, in some embodiments, the outer zone of material 240 may extend proximally from the distal end 16 of the guidewire for about 15 cm or less, about 10 cm or less, about 5 cm or less, or about 3 cm or less. In some embodiments, the thickness of the outer zone of material 240 may be about 2 nanometers or more, about 5 nanometers or more, about 10 nanometers or more, about 25 nanometers or more, or about 50 nanometers or more, for example. In some embodiments, the thickness of the outer zone of material 240 may be about 2 micrometers or less, about 1 micrometer or less, about 500 nanometers or less, about 100 nanometers or less, about 50 nanometers or less, about 25 nanometers or less, or about 10 nanometers or less, for example. In some embodiments, the thickness of the outer zone of material 240 may be in the range of about 2 nanometers to about 2 micrometers, in the range of about 2 nanometers to about 1 micrometer, in the range of about 2 nanometers to about 500 nanometers, in the range of about 2 nanometers to about 100 nanometers, in the range of about 5 nanometers to about 1 micrometer, in the range of about 5 nanometers to about 500 nanometers, or in the range of about 5 nanometers to about 100 nanometers, for example. Although some suitable dimensions are disclosed, one of skill in the art, incited by the present disclosure, would understand desired dimensions may deviate from those expressly disclosed.

The outer zone of material 240 may be any of various materials, such as any of those discussed above, or others. For instance, the outer zone of material 240 may be a biocompatible material such as titanium or a titanium alloy, tungsten or a tungsten alloy, tantalum or a tantalum alloy, chromium or a chromium alloy, niobium or a niobium alloy, zirconium or a zirconium alloy, platinum or a platinum alloy, combinations thereof, and the like, or any other suitable material.

As shown in FIG. 2C, the inner zone of material 230 is chosen to have a coefficient of thermal expansion greater than the coefficient of thermal expansion of the outer zone of material 240. For instance, the coefficient of thermal expansion of the inner zone of material 230 may be about $10 \times 10^{-6}/°$ C. to about $18 \times 10^{-6}/°$ C., or about $10 \times 10^{-6}/°$ C. to about $14 \times 10^{-6}/°$ C., or about $10 \times 10^{-6}/°$ C. to about $12 \times 10^{-6}/°$ C., or about $14 \times 10^{-6}/°$ C. to about $18 \times 10^{-6}/°$ C., or about $16 \times 10^{-6}/°$ C. to about $18 \times 10^{-6}/°$ C. Likewise, the coefficient of thermal expansion of the outer zone of material 240 may be about $4 \times 10^{-6}/°$ C. to about $14 \times 10^{-6}/°$ C., about $6 \times 10^{-6}/°$ C. to about $12 \times 10^{-6}/°$ C., or about $8 \times 10^{-6}/°$ C. to about $10 \times 10^{-6}/°$ C., about $4 \times 10^{-6}/°$ C. to about $5 \times 10^{-6}/°$ C., about $5 \times 10^{-6}/°$ C. to about $6 \times 10^{-6}/°$ C., about $6 \times 10^{-6}/°$ C. to about $7 \times 10^{-6}/°$ C., about $7 \times 10^{-6}/°$ C. to about $8 \times 10^{-6}/°$ C., about $8 \times 10^{-6}/°$ C. to about $9 \times 10^{-6}/°$ C., or about $9 \times 10^{-6}/°$ C. to about $10 \times 10^{-6}/°$ C., for example. In some embodiments the difference between the coefficient of thermal expansion of the inner zone of material 230 and the coefficient of thermal expansion of the outer zone of material 240 may be about $2 \times 10^{-6}/°$ C. to about $10 \times 10^{-6}/°$ C., or about $2 \times 10^{-6}/°$ C. to about $4 \times 10^{-6}/°$ C., or about $4 \times 10^{-6}/°$ C. to about $5 \times 10^{-6}/°$ C., or about $5 \times 10^{-6}/°$ C. to about $7 \times 10^{-6}/°$ C., or about $7 \times 10^{-6}/°$ C. to about $9 \times 10^{-6}/°$ C., for example.

An interface 250 may be defined between the inner zone of material 230 and the outer peripheral zone of material 240 at a subsurface location of the elongate shaft 12. The outer zone of material 240 may be metallurgically or metallically bonded to the inner zone of material 230 at the interface 250. A metallurgical or metallic bond is distinguishable from other types of bonds, such as mechanical bonds, covalent bonds, and ionic bonds. A metallurgical bond is achieved when atoms of two materials interact at the atomic or molecular level such that atoms of each material share electrons with atoms of the other material, forming an electron sea. A metallurgical bond is an omnidirectional, non-polar bond which involves the delocalized sharing of free electrons among a lattice of positively charged metal atoms known as kernels. Thus, a metallurgical bond is distinguishable from a covalent or ionic bond. It is believed that an attractive force is present at the interface between the positively charged metal atoms or kernels of the bonded materials and the delocalized electrons, fusing the materials together. Dissimilarly, a mechanical bond is achieved by the interaction of the surface roughness of the bonded materials in which delocalized sharing of free electrons is not present. For example, a drawing process may result in a mechanical bond between two materials. Materials joined by a mechanical bond may be amenable to separation when subjected to bending, whereas materials which are metallurgically bonded may remain bonded together when subjected to bending. This may be explained by the fact that the positively charged cations, called kernels, may shift around on the layer of electrons, but because of the delocalized nature of the electrons, the omnidirectional bonds will not break.

The outer zone of material 240 may be metallurgically bonded to the inner zone of material 230 in various ways. For example, the outer zone of material 240 may be metallurgically bonded to the inner zone of material 230 through a physical vapor deposition process, a chemical vapor deposition process, a plasma-enhanced chemical vapor deposition process, a cold spray process, a hot spray process, an electroplating process, or the like.

Figure 3A:
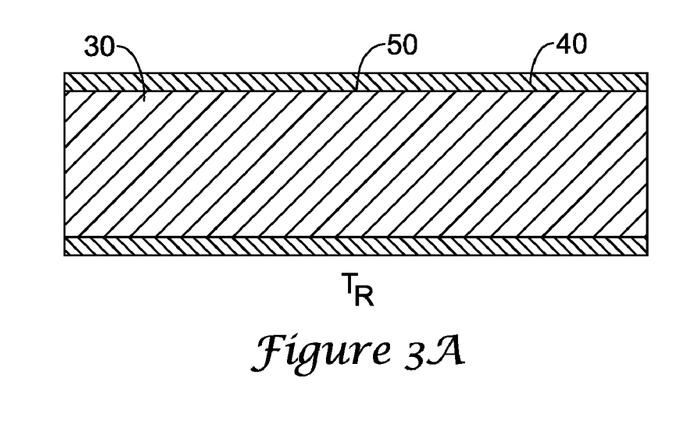
FIG. 3A is an illustrative depiction of a portion of the guidewire of FIG. 1 at a temperature $T_R$.
Figure 3B:
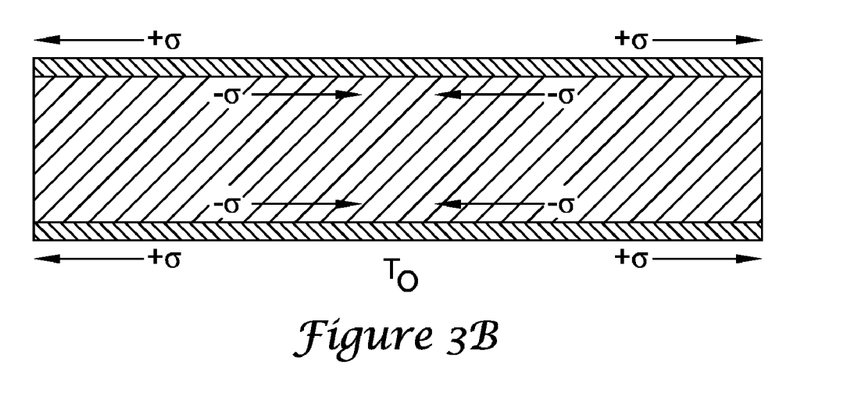
FIG. 3B is an illustrative depiction of a portion of the guidewire of FIG. 1 at a temperature $T_O$.

FIGS. 3A and 3B illustrate the mechanics of a portion of the guidewire 10 including the inner zone of material 30 having a first coefficient of thermal expansion and the outer zone of material 40 having a second coefficient of thermal expansion less than the first coefficient of thermal expansion during exemplary operating conditions. As illustrated in FIGS. 3A and 3B, the outer zone of material 40 may be metallurgically or metallically bonded to the inner zone of material 30.

FIG. 3A illustrates a portion of the guidewire 10 at a first temperature, represented as temperature $T_R$. In some embodiments the temperature $T_R$ is selected to be about room temperature. For instance, in some embodiments the temperature $T_R$ may be in the range of about 10° C. to about 25° C., or in the range of about 20° C. to about 22° C. Temperature $T_R$ may be considered to be a temperature at which point the outer zone of material 40 imparts approximately zero or otherwise negligible compressive stresses onto the inner zone of material 30 due to relative thermal expansivity of the zones of material.

FIG. 3B illustrates a portion of the guidewire 10 at a second temperature, represented as temperature $T_O$, which may be a predetermined temperature at which compressive stresses are known to be present in the inner zone of material 30 due to the relative thermal expansivity of the zones of material. In some embodiments the temperature $T_O$ is about body temperature, or other elevated or operating temperature. For instance, in some embodiments the temperature $T_R$ may be in the range of about 27° C. to about 40° C., or about 37° C., corresponding to the approximate body temperature of a human patient. Thus, the second temperature, temperature $T_O$, may be greater than the first temperature, temperature $T_R$.

It is noted that these temperatures are provided by way of example, and one of skill in the art, incited by the present disclosure, would understand other temperatures may apply in which the second temperature, $T_O$, is greater than the first temperature, $T_R$. Thus, one skilled in the art would understand that the temperature $T_O$ and/or the temperature $T_R$ may be any desired temperatures in which the temperature $T_O$ is greater than the temperature $T_R$, thus providing a temperature differential between the temperature $T_O$ and the temperature $T_R$.

By selecting the inner zone of material 30 to have a greater coefficient of thermal expansion than the outer zone of material 40, as the temperature of the portion of the guidewire 10 increases, compressive stress is imparted to the inner zone of material 30 at a subsurface location proximate the interface 50 between the inner zone of material 30 and the outer zone of material 40. This may be due to the propensity of the inner zone of material 30 to thermally expand (e.g., longitudinally and/or radially) at a greater rate than the outer zone of material 40 surrounding the inner zone of material 30. However, the metallurgical or metallic bond between the inner zone of material 30 and the outer zone of material 40 inhibits free thermal expansion (e.g., longitudinal and/or radial) of the inner zone of material 30. Thus, the outer zone of material 40, opposes free thermal expansion of the inner zone of material 30, creating residual compressive stresses in the inner zone of material 30 proximate the interface 50 between the inner zone of material 30 and the outer zone of material 40. Therefore, compressive stresses are imparted in the guidewire 10 at a subsurface location of the guidewire 10 proximate the interface 50 when the guidewire 10 is used within a human body, for instance.

The residual compressive stress imparted into the inner zone of material 30 may be estimated by the equation:

$$\sigma = E/(1-v) \times \Delta T \times \Delta \alpha$$

wherein:
- E=Young's modulus of the inner zone of material 40
- v=Poisson's ratio of the inner zone of material 40
- $\Delta T$=the change in temperature between $T_O$ and $T_R$
- $\Delta \alpha$=the difference between the coefficient of thermal expansion of the outer zone of material 40 and coefficient of thermal expansion of the inner zone of material 30

Thus, the residual compressive stress imparted into the inner zone of material 30 at an operating temperature (e.g., at a second temperature greater than a first temperature in which residual compressive stresses are negligible) due to the relative thermal expansivity of the zones of material may be directly proportional to the difference between the coefficient of thermal expansion of the inner zone of material 30 and the coefficient of thermal expansion of the outer zone of material 40. In some embodiments the residual compressive stress imparted into the inner zone of material 30 at the second or operating temperature $T_O$ may be in the range of between about 1 MPa to about 300 MPa, in the range of between about 2 MPa to about 5 MPa, in the range between about 5 MPa to 20 MPa, in the range between about 20 MPa to about 30 MPa, in the range between about 25 MPa to about 35 MPa, or in the range of between about 35 MPa to about 40 MPa, for example. Although some suitable values are disclosed, one of skill in the art, incited by the present disclosure, would understand desired values may deviate from those expressly disclosed depending on material selection.

Figure 4A:
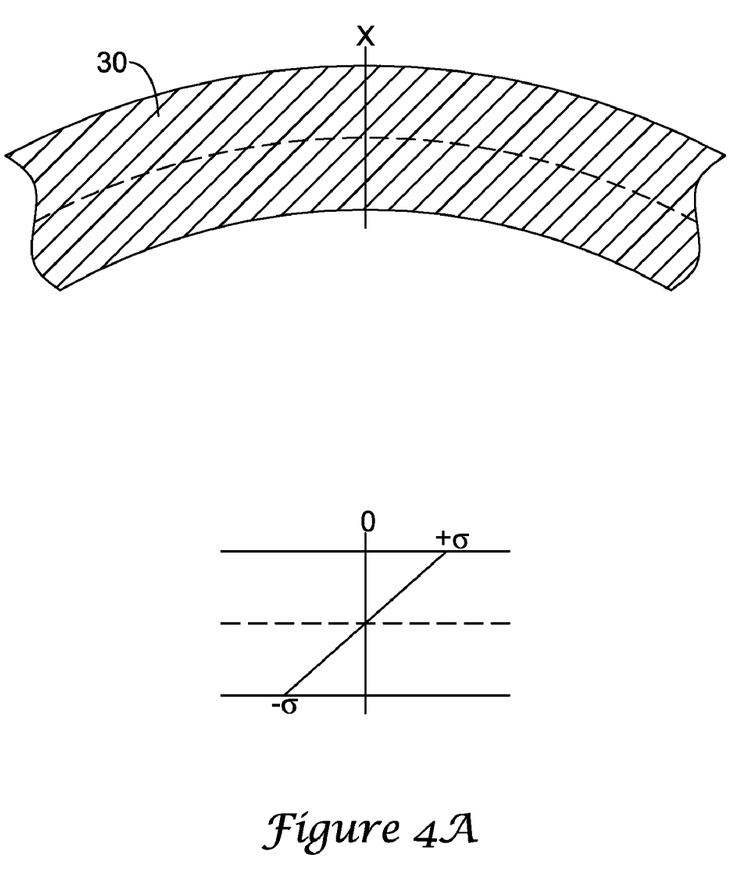
FIG. 4A shows illustrative in-plane stress levels of a conventional guidewire in bending.

FIG. 4A illustrates a portion of a guidewire including only the inner zone of material 30 at a given magnitude of bending at a temperature $T_O$. The guidewire depicted in FIG. 4A is without an outer zone of material. As shown in the diagram accompanying the illustrated portion of the guidewire, the in-plane bending tensile stresses experienced by the guidewire are at their maximum at the convex side of the bend of the guidewire and at their minimum at the concave side of the bend of the guidewire. Note, $+\sigma$ represents tensile stress and $-\sigma$ represents compressive stress.

As used herein, the "convex side of the bend" is intended to refer to the outer surface or radially outward most surface of the curvature of the bend of the guidewire, which would be known by one skilled in the art as having the greatest bending tensile stress. As used herein, the "concave side of the bend" is intended to refer to the inner surface or radially inward most surface of the curvature of the bend of the guidewire, which would be known by one skilled in the art as having the greatest bending compressive stress.

Thus, when the guidewire is subjected to bending at a temperature $T_O$, the largest in-plane bending tensile stress is located at the convex side of the guidewire (i.e., radially outward most surface of the curvature of the bend of the guidewire) and the largest in-plane compressive stress is located at the concave side of the guidewire (i.e., at the radially inward most surface of the curvature of the bend of the guidewire).

Figure 4B:
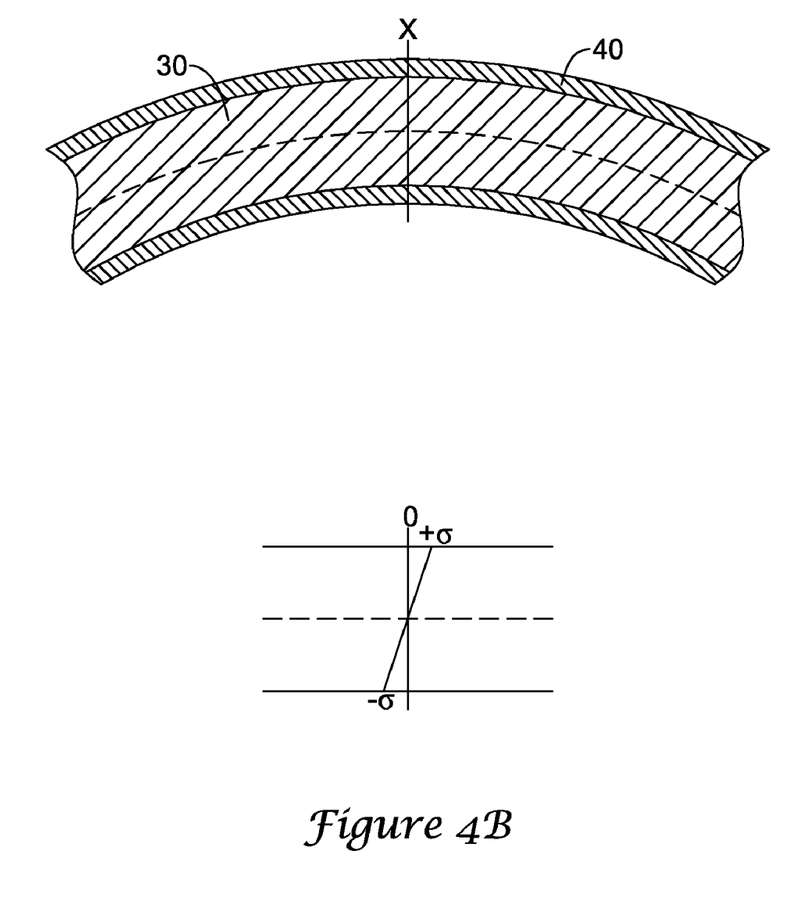
FIG. 4B shows illustrative in-plane stress levels of the guidewire of FIG. 1 in bending.

FIG. 4B illustrates a portion of the guidewire 10 at the same magnitude of bending as the guidewire without an outer zone of material shown in FIG. 4A. The guidewire 10 includes an inner zone of material 30 having a first coefficient of thermal expansion surrounded by an outer zone of material 40 having a second coefficient of thermal expansion less than the first coefficient of thermal expansion as taught herein. The illustrated portion of the guidewire 10 is exposed to a temperature $T_O$ in which residual compressive stresses are introduced in the inner zone of material 30. As shown in the diagram accompanying the illustrated portion of the guidewire 10 as taught herein, the in-plane bending tensile stresses experienced by the guidewire 10 are less than those shown in FIG. 4A of a guidewire without an outer zone of material 40. Thus, the residual compressive stresses induced in the inner zone of material 30 at the elevated temperature by the inclusion of the outer zone of material 40 oppose in-plane tensile bending stresses resultant of the bending of the guidewire 10, therefore reducing the maximum in-plane bending stress experienced by the guidewire 10 at a specified magnitude of bending. In some instances, at a temperature $T_O$, the maximum in-plane bending stress experienced by the guidewire 10 may be greatly reduced or even eliminated at some degrees of applied bending force.

Figure 5:
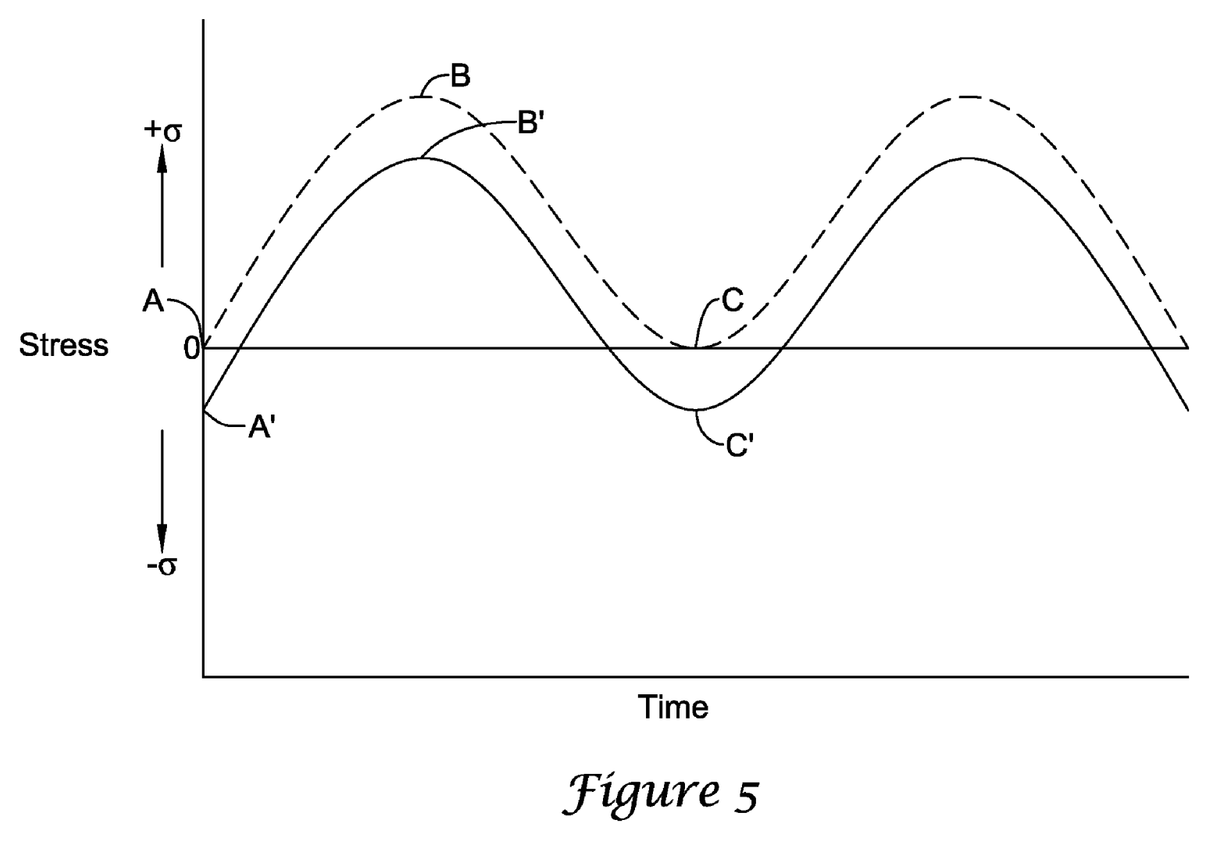
FIG. 5 is a graph comparing illustrative in-plane cyclic stress levels of the guidewire of FIG. 1 to illustrative in-plane cyclic stress levels of a conventional guidewire.

FIG. 5 is a graph illustrating representative cyclic stresses which may be experienced by a guidewire at a convex side of the guidewire during bending at an elevated or operating temperature, such as temperature $T_O$. The solid line shown on the graph identifies representative cyclic stresses of the guidewire 10 taught herein compared to representative cyclic stresses of a conventional guidewire shown in dashed lines. As shown in FIG. 5, at point A, a conventional guidewire exhibits about zero bending stress when not subjected to bending. As the conventional guidewire is subjected to a given amount of bending, the convex side of the conventional guidewire experiences a maximum bending tensile stress at point B. As the guidewire concludes one cycle of bending at which point the conventional guidewire is again not subjected to bending, the conventional guidewire once again exhibits about zero bending stress at point C. This cycle may be repeated until fatigue failure of the conventional guidewire is reached. The number of cycles that the conventional guidewire undergoes before fatigue failure is called the fatigue life of the conventional guidewire.

The solid line shown on the graph of FIG. 5 is representative of the guidewire 10 illustrated in FIG. 1 at an elevated or operating temperature, such as temperature $T_O$. At the temperature $T_O$, residual compressive stress is present in the inner zone of material 30 due to the relative thermal expansivity of the zones of material of the elongate shaft 12. Thus, when the guidewire 10 is not subjected to bending, the guidewire 10 experiences an amount of compressive stress at point A'. As the guidewire 10 is subjected to a given amount of bending (the same magnitude as the conventional guidewire represented by the dashed lines), the convex side of the guidewire 10 experiences a maximum bending tensile stress at point B'. As noted in FIG. 5, the maximum bending tensile stress experienced by the guidewire 10 is less than the maximum bending tensile stress experienced for the conventional guidewire for a given degree of bending. Thus, the residual compressive stress imparted in the inner zone of material 30 reduces the maximum bending tensile stress experienced by the guidewire 10 at a given degree of bending. As the guidewire 10 concludes one cycle of bending, the net stress experienced by the guidewire becomes compressive, and at point C', at which point the guidewire 10 is no longer subjected to bending, the guidewire 10 exhibits the residual compressive stress imparted in the inner zone of material 30 due to the relative thermal expansivity of the zones of material of the elongate shaft 12 at temperature $T_O$.

Thus, the residual compressive stress imparted in the inner zone of material 30 shifts the stress curve of the guidewire 10 downward by an amount equal to the magnitude of the residual compressive stress of the inner zone of material 30 at an elevated or operating temperature, such as temperature $T_O$. The residual compressive stress bestowed on the inner zone of material 30 may inhibit and/or prevent crack initiation and/or propagation within the inner zone of material 30. Because the maximum bending tensile stress experienced by the guidewire 10 at $T_O$ is reduced, the fatigue life of the guidewire 10 may be extended. Thus, in instances where the guidewire 10 experiences cyclic bending, such as when subjected to bending forces attributed to the rhythmic movement of a beating heart, the fatigue life of the guidewire 10 may be extended.

A further advantage of the disclosed outer zone of material 40 surrounding an inner zone of material 30 is the ability of the outer zone of material 40 to prevent direct contact of an aqueous fluid on the inner zone of material 30, which may otherwise compromise or reduce the fatigue life of the guidewire. Additionally, the outer zone of material 40 may inhibit or prevent any detrimental effects of possible surface defects of the inner zone of material 30 which may otherwise compromise or reduce the fatigue life of the guidewire.

In some embodiments, the exterior surface of the guidewire 10 (including, for example, the exterior surface of the outer zone of material 40) may include a coating, for example a lubricious, a hydrophilic, a protective, or other type of coating may be applied over portions or all of the guidewire 10. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

Figures 6, 6A:
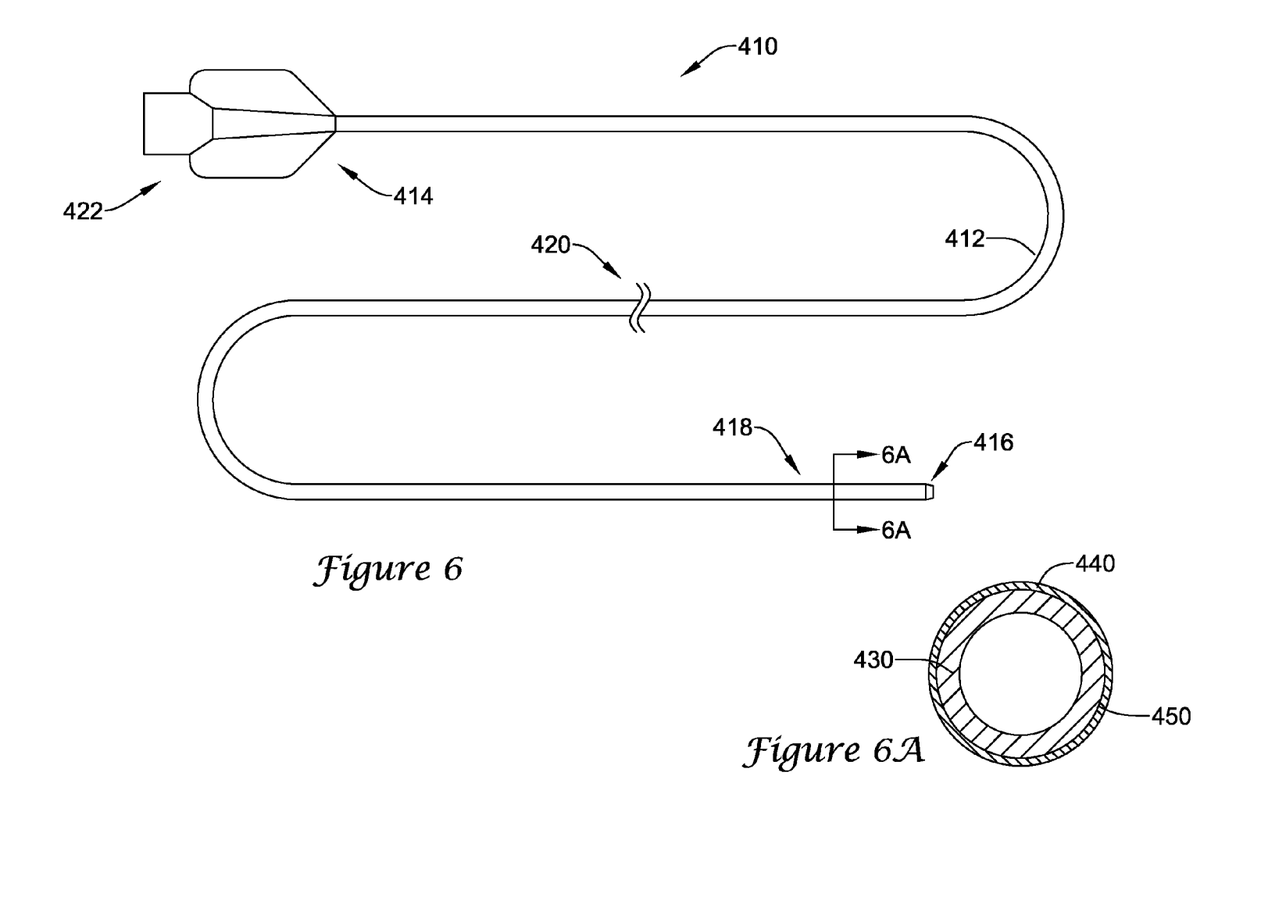
FIG. 6 is a plan view of an exemplary catheter.
FIG. 6A is a cross-sectional view of a portion of the catheter of FIG. 6 taken along line 6A-6A of FIG. 6.

FIG. 6 illustrates an exemplary catheter 410 characteristic of aspects described herein. The catheter 410 is illustrated as a micro catheter. However, in other embodiments, the catheter 410 may be a guide catheter, an angioplasty catheter, a perfusion catheter, or other catheter known in the art. The catheter 410 includes an elongate shaft 412 having a proximal end 414 and a distal end 416. The catheter 410 may include a distal portion 418 proximate the distal end 416 and a proximal portion 420 proximal of the distal portion 418. The catheter 410 may additionally include a hub assembly 422 attached to the elongate shaft 412 proximate the proximal end 414 of the elongate shaft 412.

FIG. 6A is an exemplary cross-section of the distal portion 418 of the catheter 410 taken along a plane perpendicular to the longitudinal axis of the catheter 410 along line 6A-6A of FIG. 6. Similarly to the guidewire 10, described above, the catheter 410 may include an inner zone of material 430 surrounded by an outer zone of material 440. The inner zone of material 430 may be metallurgically or metallically bonded to the outer zone of material 440 along an interface 450 at a subsurface location between the inner zone of material 430 and the outer zone of material 440. The inner zone of material 430 may be chosen to have a coefficient of thermal expansion greater than the coefficient of thermal expansion of the outer zone of material 440. Thus, at an elevated temperature, such as temperature $T_O$, in which residual compressive stresses are imparted in the inner zone of material 430 due to the relative thermal expansivity of the zones of material, when the catheter 410 is subjected to an applied bending tensile stress, the compressive stress exerted on the inner zone of material 430 by the outer zone of material 440 opposes the applied bending tensile stress, thereby reducing the maximum bending tensile stress experienced by the inner zone of material 430.

Figure 7:
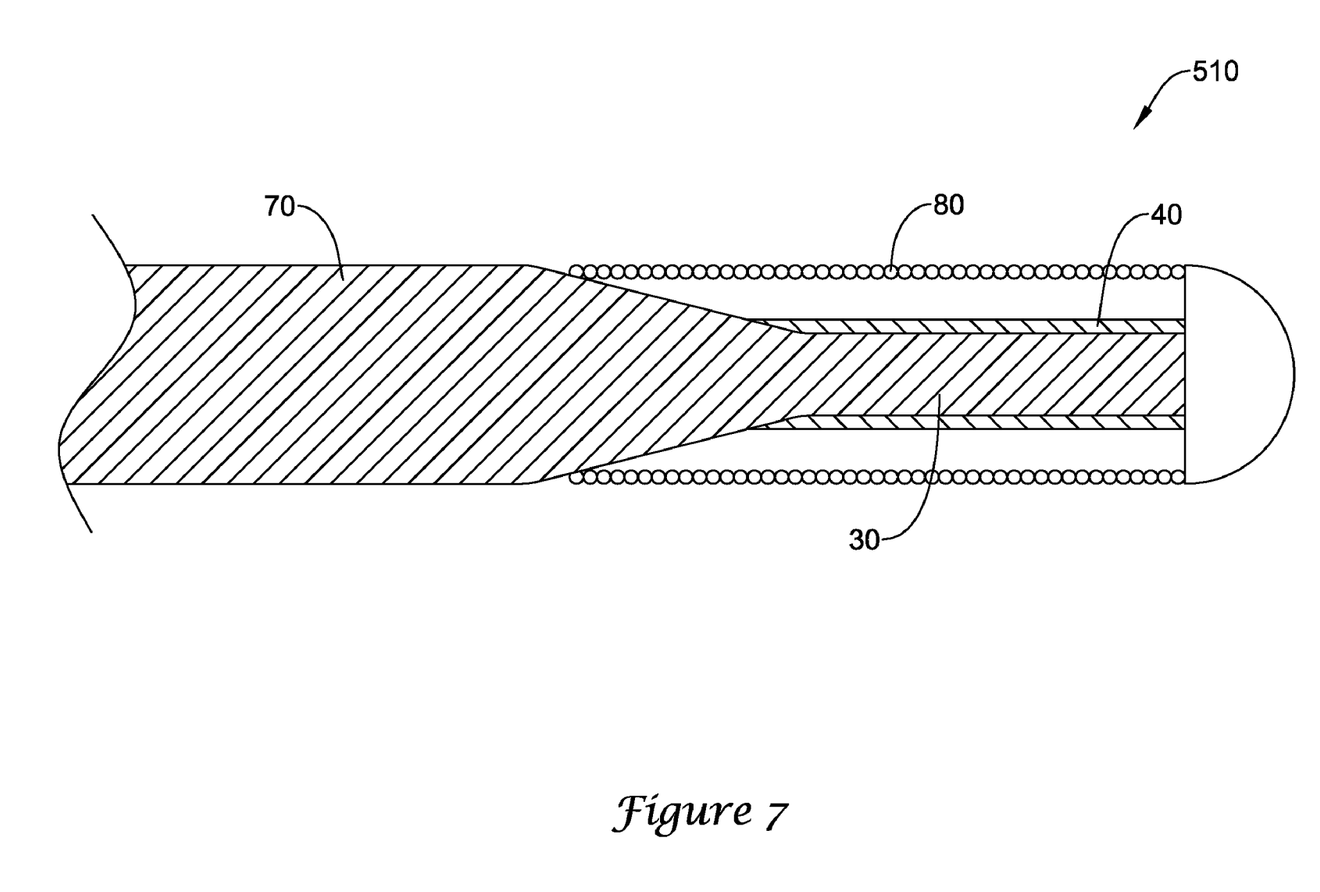
FIG. 7 is a cross-sectional view of the distal portion of an exemplary guidewire.
Figure 8:
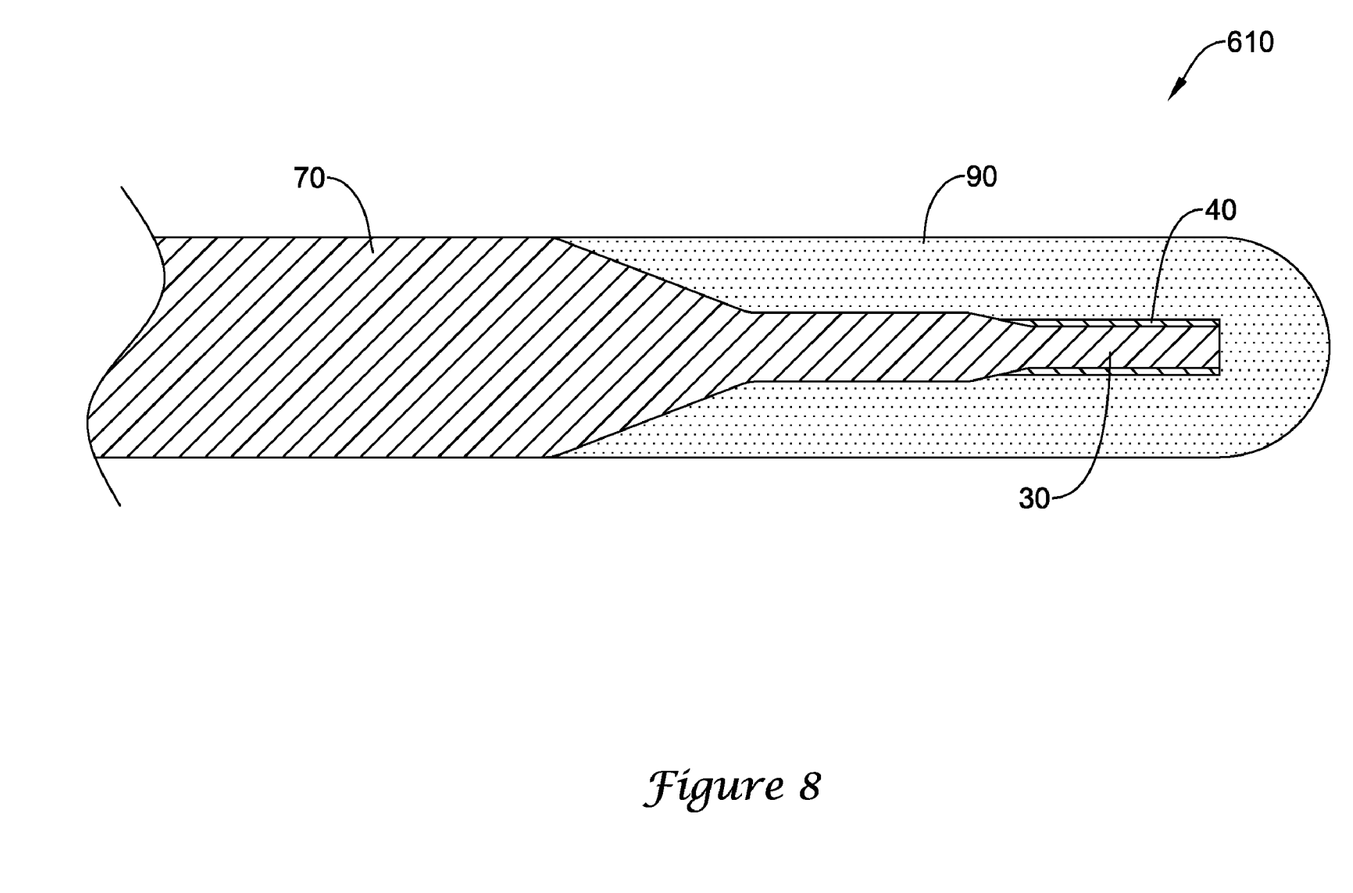
FIG. 8 is a cross-sectional view of the distal portion of another exemplary guidewire.

It is noted that structures disclosed herein could be used as components of various medical devices. For example, as shown in FIGS. 7 and 8, the disclosed structures may be used as a core wire of a guidewire. One possible guidewire structure, shown in FIG. 7, depicts the distal portion of a guidewire 510 including a core wire 70 and a coil tip 80, such as a spring coil tip, disposed over a distal reduced diameter portion of the core wire 70. The reduced diameter portion of the core wire 70 may include an inner zone of material 30 and an outer zone of material 40 as described herein. Another possible guidewire structure, shown in FIG. 8, depicts the distal portion of a guidewire 610 including a core wire 70 and a polymer jacket 90 disposed over a distal reduced diameter portion of the core wire 70. The reduced diameter portion of the core wire 70 may include an inner zone of material 30 and an outer zone of material 40 as described herein.

Additionally, the construction of the guidewire may include other components such as spring tips, coiled members, marker members, polymer tips and/or members, shaping structures or the like. Some examples of guidewire constructions that may include a core wire including the structures disclosed herein may include U.S. Pat. Nos. 7,074, 197 and 7,182,735, which are incorporated herein by reference. Also, such constructions as disclosed herein may be used in other medical devices, such as distal protection devices, fixed wire devices, drive shafts for rotational devices, embolic protection devices, endoscopic devices, laproscopic devices, or the like.

Those skilled in the art will recognize that the present invention may be manifested in a variety of forms other than the specific embodiments described and contemplated herein. For example, other medical devices, such as stents, sheaths, filter wires, or the like, may also employ similar characteristics as described herein. Accordingly, departure in form and detail may be made without departing from the scope and spirit of the present invention as described in the appended claims.

What is claimed is:

1. A medical guidewire having a proximal end, a distal end and an outer surface extending between the proximal end and the distal end, the medical guidewire comprising:
   an inner zone of material, the inner zone of material having a coefficient of thermal expansion; and
   an outer peripheral zone of material fully encircling the inner zone of material;
   wherein the outer peripheral zone of material is metallurgically bonded to the inner zone of material along an interface between the inner zone of material and the outer peripheral zone of material, the outer peripheral zone of material having a coefficient of thermal expansion less than the coefficient of thermal expansion of the inner zone of material.

2. The medical guidewire of claim 1, wherein at a first temperature the outer peripheral zone of material exerts approximately zero or negligible residual compressive stress on the inner zone of material, and at a second temperature greater than the first temperature the outer peripheral zone of material exerts a residual compressive stress on the inner zone of material.

3. The medical guidewire of claim 2, wherein the first temperature is in the range of about 10° C. to about 25° C., and the second temperature is in the range of about 27° C. to about 40° C.

4. The medical guidewire of claim 1, wherein when the guidewire is subjected to an applied bending tensile stress at an elevated temperature, the compressive stress exerted on the inner zone of material by the outer peripheral zone of material opposes the applied bending tensile stress, thereby reducing the maximum bending tensile stress experienced by the inner zone of material.

5. The medical guidewire of claim 1, wherein at a temperature in the range of about 27° C. to about 40° C. the outer peripheral zone of material opposes expansion of the inner zone of material such that the outer peripheral zone of material exerts a compressive stress on the inner zone of material at a subsurface location of the guidewire.

6. The medical guidewire of claim 1, wherein at a temperature in the range of about 27° C. to about 40° C. the inner zone of material has a residual compressive stress.

7. The medical guidewire of claim 6, wherein the residual compressive stress is in the range of between about 1 MPa to about 300 MPa.

8. A method of increasing the fatigue life of a medical guidewire, the method comprising:
    providing a guidewire including an inner zone of material having a first coefficient of thermal expansion, and an outer peripheral zone of material having a second coefficient of thermal expansion less than the first coefficient of thermal expansion;
    wherein the outer peripheral zone of material fully encompasses the inner zone of material; and
    exposing the guidewire to an operating temperature wherein the outer peripheral zone of material opposes expansion of the inner zone of material such that the outer peripheral zone of material exerts a compressive stress on the inner zone of material.

9. The method according to claim 8, wherein when the guidewire is subjected to an applied bending tensile stress at the operating temperature, the compressive stress exerted on the inner zone of material by the outer peripheral zone of material opposes the applied bending tensile stress, thereby reducing the maximum bending tensile stress experienced by the inner zone of material.

10. The method according to claim 8, further comprising the step of metallurgically bonding the outer peripheral zone of material to the inner zone of material.

11. The method according to claim 8, further comprising the step of molecularly modifying the inner zone of material to generate the outer peripheral zone of material.

12. A method of increasing the fatigue life of a medical guidewire, the method comprising:
    providing an elongate shaft including a first material having a first coefficient of thermal expansion;
    metallurgically bonding a second material to the first material, the second material having a second coefficient of thermal expansion less than the first coefficient of thermal expansion; such that at a first temperature the second material exerts approximately zero or negligible compressive stresses on the first material, and at a second temperature greater than the first temperature the second material opposes expansion of the first material, thereby exerting a compressive stress on the first material.

13. The method according to claim 12, wherein the first temperature is in the range of about 10° C. to about 25° C.

14. The method according to claim 12, wherein the second temperature is in the range of about 27° C. to about 40° C.

* * * * *